US005496537A

United States Patent [19]

Henry

[11] Patent Number: 5,496,537

[45] Date of Patent: Mar. 5, 1996

[54] PROPOFOL HYDROFLUOROCARBON PROPELLANT FORMULATIONS

[76] Inventor: Richard A. Henry, 7 Toronto Street, Kingston, Ontario, Canada, K7L 4A3

[21] Appl. No.: 408,866

[22] Filed: Mar. 23, 1995

[51] Int. Cl.$^6$ .......... A61K 9/12

[52] U.S. Cl. .......... 424/45; 424/46; 514/818; 514/974

[58] Field of Search .......... 424/45, 47, 46; 514/818, 974

[56] References Cited

U.S. PATENT DOCUMENTS

| | | | |
|---|---|---|---|
| 5,118,494 | 6/1992 | Schultz et al. | 424/45 |
| 5,190,029 | 3/1993 | Byron et al. | 424/45 |
| 5,225,183 | 6/1993 | Purewal et al. | 424/45 |

FOREIGN PATENT DOCUMENTS

| | | | |
|---|---|---|---|
| 07333 | 7/1990 | WIPO | 424/45 |

OTHER PUBLICATIONS

Kanto, J. H., "Propofol, the newest induction agent of anesthesia" *International Journal of Clinical Pharmacology,* vol. 26 No. 1 1988 (pp. 41–57).

Gennaro, A. R. (1985). Remington's Pharmaceutical Sciences (17th ed.). Mack Publishing Co., pp. 1670–1677.

Morén, F. et al. (1993). Aerosols in Medicine. Principles, Diagnosis and Therapy. Elsevier Sci. Publishers, pp. 303–319.

Jakobsson, J. et al. (1995). Acta Anaesthesiologica Scandanavica 39(4): 503–507.

*Primary Examiner*—Thurman K. Page
*Assistant Examiner*—Raj Bawa
*Attorney, Agent, or Firm*—Whitham, Curtis, Whitham, & McGinn

[57] ABSTRACT

Non-volatile general anesthetics are advantageously provided to patients in aerosolized form using a metered dose inhaler. The anesthetics are highly lipophilic in character and are rapidly absorbed through the nasal, oral, and lung mucosa. Experiments have shown that propofol is readily soluble in hydrofluorocarbon propellants without the use of surfactants and co-solvents. The solubility allows for the controlled delivery of concentrated pure anesthetic agents like propofol to the airway mucosa of human and animal patients to cause rapid onset of sedation or anesthesia without the requirement of prior intravenous access.

5 Claims, No Drawings

PROPOFOL HYDROFLUOROCARBON PROPELLANT FORMULATIONS

DESCRIPTION

BACKGROUND OF THE INVENTION

1. Field of the Invention

The invention is related to general anesthetics and, more particularly, to aerosol formulations of general anesthetic agents that are liquid or solid at room temperature and are ordinarily administered intravenously, and the aerosolized delivery of these agents to the nasal, oral, and/or lung mucosa via patient inhalation.

2. Description of the Prior Art

A local anesthetic agent is a compound that reversibly depresses neuronal function, which results in a loss of the patient's ability to perceive pain and/or other sensations. A general anesthetic is one which causes a patient to lose consciousness. This type of agent is often referred to as a "hypnotic" agent. Nitrous oxide, which is often referred to as "laughing gas", is an example of an inhaled general anesthetic which is in common use. Halothane, isoflurane, and enflurane are examples of more potent, inhaled volatile general anesthetics that ante administered as a gas.

A number of hypnotic agents are also administered as an injected liquid solution or emulsion, as opposed to a gas. These agents are typically quick acting and may have desired analgesic properties, as well as advantageous systemic clearance properties upon termination of administration. These agents are ordinarily a liquid or solid at room temperature and have not, prior to this invention, been administered by aerosol.

Propofol, 2,6-diisopropylphenol ($C_{12}H_{18}O$), is one example of a rapidly acting hypnotic agent that is used as an intravenous general anaesthetic. It produces rapid and smooth induction of anaesthesia in one arm-brain circulation time, with good cardiovascular stability and a rapid and good quality of recovery with freedom from nausea.

Propofol in its pure form is a colorless liquid at room temperature (melting point 19° C.). It is practically insoluble in water, thus it is difficult to formulate into a water soluble preparation suitable for intravenous administration. It was first used as a 1% active solution in 16% cremaphor EL as a solubilizing agent. When it became evident that cremaphor EL was associated with a significant risk of hypersensitivity reactions it was withdrawn from the market. Later it was reformulated in a soya bean oil emulsion: 1% weight in volume (w/v) aqueous emulsion in 10% w/v soya bean oil, 1.2% egg phosphatide, and 2.5% glycerol (see, Kanto, *J. Clin. Pharm., Ther. Tox.*, Vol. 26, No. 1, 1988, pp.41–57). This reformulation overcame the solubility problem and provided a safer solubilizing technique than was achieved with cremaphor EL. The principle disadvantages of the reformulated product are a slight pain to the patient upon injection, and a short shelf-life, especially after opening the vial, owing to its susceptibility to contamination.

Propofol has many advantageous kinetic properties explaining its usefulness when administered by bolus dose intravenously for induction of anesthesia (1–2.5 mg/kg), including very rapid distribution, rapid elimination and high systemic clearance. A continuous infusion (75– 300 μg/kg/min) will maintain anesthesia as part of a balanced or a total intravenous anaesthetic; characterized by a rapid recovery on cessation of the infusion. These desirable kinetic properties are attributed to the high lipid solubility of this drug and its rapid metabolism. Infusions of sub-anesthetic doses (25–100 μg/kg/min) of propofol can be used to provide sedation for patients undergoing procedures under local anesthesia or patients in intensive care on ventilatory support. The infusion allows rapid and easy control of the level of sedation and blood pressure. The rapid recovery of consciousness after the cessation of the infusion is an advantageous property of propofol.

Anesthetic and sedative techniques used in the ambulatory setting preferably have a low incidence of postoperative side effects, thus ensuring an optimum patient safety by allowing a rapid return to pre-operative status. Propofol's predictable recovery and favorable side effect profile; even after repeated bolus doses or a titrated continuous infusion, make it well suited for induction and maintenance of anesthesia or sedation during short ambulatory procedures.

In the pediatric patient population, intravenous induction of anesthesia remains a problem because of the difficulty in obtaining vascular access in the awake and frightened child. Inhalational anaesthesia using potent volatile anesthetic agents such as halothane are routinely used for induction of anesthesia in many situations in order to avoid the need for intravenous access before the child is asleep. Alternatively, a sedative agent can be administered. Sedation needs to administered ahead of time as onset of action is slow. The use of sedative agents requires the child to be observed until the anesthetic is given and it prolongs the recovery time after a short procedure. Intranasal midazalam using the water-soluble intravenous preparation has recently been advocated. It has the disadvantages of stinging on administration, slow onset time and a slow recovery.

SUMMARY OF THE INVENTION

It is an object of this invention to provide rapid acting, general anesthetic compounds, that have desirable recovery and clearance properties, but which are ordinarily administered intravenously and are either a liquid or solid at room temperature, to a patient via aerosol inhalation (nasal and/or oral), instead of by injection.

It is another object of this invention to provide aerosol formulations of rapid acting, general anesthetic compounds, that have desirable recovery and clearance properties, but which are ordinarily administered intravenously and are either a liquid or solid at room temperature (e.g., 23°–28° C.).

It is yet another object of this invention to provide novel aerosol formulations which include propofol and hydrofluorocarbon propellants.

According to the invention, it has been discovered that propofol forms a stable solution with hydrofluorocarbon propellants such as 1,1,1,2-tetrafluoroethane. The solution is spontaneously formed, and does not require the presence of surfactants or solvents. An aerosol formulation containing propofol can be administered to the nasal, oral, or lung mucosa by patient inhalation, and provides rapid onset of unconsciousness and/or sedation. The invention demonstrates that traditional intravenous general anesthetics that are non-volatile at room temperature can be administered safely and effectively as an aerosol, and provides a particular aerosol formulation containing propofol which utilizes "ozone friendly" propellants.

DETAILED DESCRIPTION OF THE PREFERRED EMBODIMENTS OF THE INVENTION

Propofol is a highly lipid-soluble substance which is a light oil at room temperature. It is insoluble in water and thus not suitable for use in an aqueous suspension. It would be advantageous to deliver propofol in its pure lipid soluble form to the airway mucosa to effect rapid and transient hypnosis. The aerosol preparation needs to be non-irritating and is required to deliver a sufficiently large enough dose to effect hypnosis or sedation. This would allow non-invasive and rapid provision of sedation and hypnosis in humans and animals.

This invention is particularly directed to the aerosolized delivery of the intravenous general anesthetic propofol to a patient using a metered dose inhaler; however, it should be understood that the invention has general application to aerosolized delivery of other intravenous general anesthetics, such as ketamine, pregnanelone, althesin, pentothal, brietal, etc., and other aerosol producing devices, such as nebulizers, dry powder inhalers, etc. In addition, dosing the intravenous general anesthetic by means other than a metering valve can be used in the practice of this invention.

Metered dose inhaler's (MDIs) have been used for several years in the treatment of chronic disorders such as asthma, In these treatment schemes, the patient is provided with a canister of medicament (e.g., albuterol, triamcinolone, beclomethasone dipropionate, etc.) which is packaged under pressure together with propellants or propellant blends. Typically, solvents, surfactants, anti-oxidants, lubricants, preservatives, and the like are packaged together with the medicament and propellant to assist in solubilizing or uniformly dispersing the medicament within the propellant, and for assuring that the mixture passes easily through a metering valve. Periodically, the patient will self-administer a dose of the medicament by actuating a metering valve connected to the canister and inhaling the medicament as it is directed out of the canister by the propellant.

This invention proposes that the MDI could be advantageously used in the delivery of anesthesia to a patient. Anesthetizing a patient is quite different from the treatment of a chronic disorder. For example, anesthesia must always be handled by a licensed professional, and anesthesia may only be administered once or a few times during the course of a surgical operation or procedure. However, the portability of an MDI canister, together with the highly accurate dose delivery afforded by an MDI, will provide an anesthetist with significant advantages. The requirement of prior intravenous access is obviated and the delay caused by needle/syringe usage is eliminated. Advantages in countries and situations where needles and syringes are difficult to keep on hand, such as during military conflicts and in poorer third world countries, are also realized. Further, aerosolized delivery of anesthetics would be advantageous in vetinary medicine since it would allow sedation or anesthesia of frightened animals to be achieved rapidly and non-invasively.

MDIs have traditionally utilized chlorofluorocarbon or "freon" propellants. World-wide treaties have called for a ban on these propellants due to their alleged impact on the earth's ozone layer. The most widely recognized CFC alternatives are hydrofluorocarbon (HFC) propellants, such as 1,1,1,2-tetrafluoroethane and 1,1,1,2,3,3,3-heptafluoropropane, and these propellants have been readily adopted in the refrigeration, polymer foam blowing, and electronic cleaning industries. However, HFC propellants have been found to behave differently than CFC propellants in the MDI environment. In particular, it has been found to be very difficult to solubilize or disperse pharmaceuticals in HFCs. Without solubilization or uniform dispersability in the propellant, the MDI cannot provide a reproducible and efficacious dose of medicament. Much work has been performed in the area of designing new surfactants and identifying co-solvents that can be used to solubilize or disperse pharmaceuticals in HFC propellants.

To date, no MDI pharmaceutical products that utilize HFC propellants have been approved for use by any industrialized country. Although, reports on recent submissions to regulatory agencies suggest that 1,1,1,2-tetrafluoroethane and 1,1,1,2,3,3,3-heptafluoroethane based MDIs are the most likely CFC-alternative MDIs to gain approval in the near future. Alternatively, the MDI industry may be successful in obtaining an exemption to current treaties which will permit the sale of CFC based MDI products.

With particular respect to propofol formulations, the inventor has discovered that propofol quickly and spontaneously solubilizes in 1,1,1,2-tetrafluoroethane (HFC-134a) and 1,1,1,2,3,3,3-heptafluoroethane (HFC-227). For example, an aerosol solution was prepared by weighing out 500 milligrams of pure propofol oil into a clean glass container and capping it with a standard valve. Five grams of HFC-134a was added with a pressure fill technique into the container. The two substances were found to produce a homogenous solution that did not separate out on standing or cooling. The container was then slowly opened to atmospheric pressure and the HFC-134a slowly released until it reached atmospheric pressure. The container was weighed again and found that there was a weight gain of 1500 milligrams. The remaining substance was present in the form of a clear oily solution and showed no signs of separating or crystal precipitation. The oily solution is essentially a new composition of matter since a portion of the HFC component remains associated with the propofol under conditions where the HFC component is normally volatile. The HFC component of the solution was readily released from the solution by adding water or alcohol (e.g., ethyl alcohol).

These experiments demonstrate that an aerosol formulation of propofol can be readily prepared using HFC propellants due to its natural miscibility with these propellants. The aerosol formulation will preferably contain 1–40% w/w propofol base dissolved in 60–99% HFC propellant or HFC propellant blend (e.g., HFC-134a, HFC-227, or a combination thereof). Due to the solubility of propofol in HFC propellants, solvents and surfactants are not necessary components of the aerosol formulation. In addition, due to the oily nature of propofol base, valve lubricants and the like are not necessary components of the aerosol formulation when it is packaged in an MDI. Propofol in its base form is preferred due to its lipophilic character which will allow ready penetration into and through the nasal, oral, and lung mucosa; however, it should be understood that other forms and derivatives of propofol may be employed.

Compounds with a similar phenolic ring structure as found in propofol, that, like propofol, also have a hydroxyl (OH) group on the ring, have been found to be insoluble in the HFC propellants on their own. For example, testing by the inventor has demonstrated metaraminol, phenylephrine, acetaminophen, salicylic acid, sodium salicylate, and methyl salicylate are insoluble, by themselves, in 1,1,1,2-tetrafluoroethane, and other sources have indicated that metaproterenol, albuterol, ritodrine, terbutaline, epinephrine, norepinephrine, and isoproterenol are also not soluble, by themselves, in 1,1,1,2-tetrafluoroethane.

The addition of taste enhancing/disguising agents in small concentrations has been found to be useful as propofol has a strong chemical taste that is unpleasant on administration. A combination which has been found to be particularly useful in combination with a propofol MDI aerosol formulation includes saccharin (a sweetener), grapefruit flavor (a flavorant), and cetylpyridinium chloride (a preservative). Other sweeteners, flavorants and preservatives, and different combinations thereof, would be useful in the practice of this invention.

Furthermore, due to the soluble character of propofol in HFCs, propofol might be used as an adjuvant (solubilizing or surfactant) in MDI formulations containing other medicaments that are not soluble HFCs. Propofol is uniquely and suprisingly highly soluble in HFC propellants, interacting with the propellants in such a way as to further alter the solubility characteristics of the propellants and allow solutions of previously insoluble or poorly soluble compounds. For example, the inventor has determined that Beta-2 agonists, such as albuterol, ritodrine, metaproterenol, terbutaline, isoetharine, and bitolterol, synthetic noncatecholamines such as phenylephrine and metaraminol, some local anesthetics such as bupivacaine, salicylates, such as salicylic acid, aspirin, sodium salicylate, and methyl salicylate, para-aminophenol derivatives such as phenacetin and acetaminophen, propionic acid derivatives such as ibuprofen, and sympathomimetics such as epinephrine, norepinephrine, isoproterenol, dopamine, dobutamine, and beta-phenylethylamine are all not soluble in HFCs without adjuvants such as surfactants and/or co-solvents. These compounds may be made to be soluble or dispersable within HFC propellants by including propofol as an adjuvant. MDIs prepared using HFC propellants and propofol as an adjuvant will preferably include 1–10% w/w medicament, 1–40% w/w propofol, and 60–98% w/w HFC propellant (preferably HFC-134a, HFC-227, and combinations thereof).

The dose of an aerosolized anesthetic can vary depending upon the patient, the result to be achieved, and the anesthetic to be aerosolized. For example, larger patients may require more anesthetic than smaller patients, more anesthetic might be required if unconsciousness is to be achieved as opposed to sedation, and different amounts of different anesthetics might be required to achieve unconsciousness or sedation. In the case of propofol, it is expected that doses ranging from 0.5–1 mg/kg be provided for achieving sedation, and doses ranging from 1–2 mg/kg be provided for achieving patient unconsciousness. These doses are comparable to doses used when propofol is administered intravenously. Because, propofol absorbs quickly, the dose delivered to the patient's airways should be comparable to an intravenous dose.

If the aerosolized anesthetic is to be provided using an MDI, the MDI canister will preferably be fitted with a metering valve which provides enough anesthetic to achieve sedation or patient unconsciousness in one or two actuations. The usual metered dose volume ranges from 25– 100 microliters, depending on the targeted delivery site. Nasal sprays are generally of the smaller volumes. The volume and concentration of the formulation are chosen to deliver the required total drug dose in the optimum droplet size and spray configuration. As the general anesthetics are highly lipid soluble, they are well absorbed from any of the airway mucosa and, therefore, droplet sizes in the respirable range (1–10 micrometers) are not necessarily required.

There is wide inter-patient variation in anesthetic requirements. Therefore, it is preferable that a single metered dose would not induce anesthesia in all but the most sensitive patients; thus, allowing the doctor to titrate the dose administered according to the effect on the patient.

The MDI canister will be filled with propellants under pressure which, when released by valve actuation, will propel the anesthetic dissolved or dispersed in the propellants into the airway of a patient for absorption through the nasal, oral, or lung mucosa. While traditional CFC propellants may be used, it is preferred that non-ozone depleting propellants such as HFCs, alkanes, and alkyl ethers be used. Surfactants and co-solvents can be combined with the anesthetic in the MDI canister as required. As noted above, in the situation where propofol is used as the anesthetic and HFCs are used as the propellant, lubricants, co-solvents, and surfactants may not be necessary.

Although the MDI is the preferred delivery device for aerosolized delivery of the general anesthetic, it should be understood that other devices such as nebulizers and the like may be advantageously used in the practice of this invention.

While the invention has been described in terms of its preferred embodiments, those skilled in the art will recognize that the invention can be practiced with modification within the spirit and scope of the appended claims.

We claim:

1. An aerosol formulation for oral or nasal delivery to a patient, consisting essentially of:

1–40% w/w propofol; and

60–99% w/w hydrofluorocarbon propellant selected from the group consisting of 1,1,1,2-tetrafluoroethane and 1,1,1,2,3,3,3-heptafluoropropane and combinations thereof.

2. The aerosol formulation of claim 1 wherein said propofol is present in its base form.

3. An aerosol formulation for oral or nasal delivery to a patient, comprising:

1–40% w/w propofol;

60–98% w/w hydrofluorocarbon propellant selected from the group consisting of 1,1,1,2-tetrafluoroethane and 1,1,1,2,3,3,3-heptafluoropropane; and 1–10% w/w of a medicament selected from the group consisting of beta-2 agonists, synthetic noncatecholamines, local anesthetic other than propofol, salicylates, para-aminophenols, propionic acids, and sympathomimetrics.

4. A method of solubilizing medicaments in hydrofluorocarbon propellants, comprising the step of using propofol at 1–40% w/w to dissolve or disperse 1–10% w/w of a medicament in 60–98% w/w of said hydrofluorocarbon propellant which is selected from the group consisting of 1,1,1,2-tetrafluoroethane and 1,1,1,2,3,3,3-heptafluoropropane.

5. An aerosol formulation as recited in claim 1 further comprising 0.1–10% by weight of a taste enhancer.

* * * * *